US010000444B2

United States Patent
Kokin

(10) Patent No.: US 10,000,444 B2
(45) Date of Patent: Jun. 19, 2018

(54) FLUORINE-CONTAINING ETHER MONOCARBOXYLIC ACID AMINOALKYL ESTER AND A METHOD FOR PRODUCING THE SAME

(71) Applicant: Unimatec Co., Ltd., Tokyo (JP)

(72) Inventor: Keisuke Kokin, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days. days.

(21) Appl. No.: 15/548,028

(22) PCT Filed: Feb. 3, 2015

(86) PCT No.: PCT/JP2015/052992
§ 371 (c)(1),
(2) Date: Aug. 1, 2017

(87) PCT Pub. No.: WO2016/125257
PCT Pub. Date: Aug. 11, 2016

(65) Prior Publication Data
US 2018/0016223 A1 Jan. 18, 2018

(51) Int. Cl.
C07C 219/06 (2006.01)
C07C 213/06 (2006.01)
C07C 213/10 (2006.01)

(52) U.S. Cl.
CPC .......... *C07C 219/06* (2013.01); *C07C 213/06* (2013.01); *C07C 213/10* (2013.01)

(58) Field of Classification Search
USPC ........................................................ 560/184
See application file for complete search history.

(56) References Cited

U.S. PATENT DOCUMENTS

| 5,606,098 | A | 2/1997 | Ryabinin et al. |
| 9,758,470 | B2 * | 9/2017 | Kokin ................... C07C 219/06 |
| 2008/0221360 | A1 | 9/2008 | Kokin et al. |
| 2012/0041201 | A1 | 2/2012 | Kokin et al. |

FOREIGN PATENT DOCUMENTS

| CN | 1955166 A | 5/2007 |
| JP | 62-270546 | 11/1987 |
| JP | 03-284642 | 12/1991 |
| JP | 10-036867 | 2/1998 |
| JP | 2008-255035 | 10/2008 |
| JP | 2008-255042 | 10/2008 |
| JP | 2009-001709 | 1/2009 |
| JP | 2010-254736 A | 11/2010 |
| JP | 2011-202055 | 10/2011 |
| JP | 2011-213837 | 10/2011 |
| JP | 2013-032455 | 2/2013 |
| WO | WO 02/26693 A1 | 4/2002 |
| WO | WO 2007/026513 A1 | 3/2007 |

OTHER PUBLICATIONS

Psathas ("Mapping the Stability and Curvature of Emulsions of H2O and Supercritical CO2 with Interfacial Tension Measurements" J. Dispersion Science and Technology, 23, p. 65-80, 2002).*
Psathas ("Interfacial Studies of the Formation of Microemulsions of Water in Carbon Dioxide with Fluorinated Surfactants" J. Dispersion Science and Technology, 23, p. 81-92, 2002).*
International Preliminary Patentability Report and Written Opinion from corresponding PCT application No. PCT/JP2015/052992 dated 008/Aug. 2017 (8 pgs).
International Search Report from corresponding PCT application No. PCT/JP2015/052992 dated Apr. 14, 2015 (4 pgs).

* cited by examiner

Primary Examiner — Jafar Parsa
Assistant Examiner — Amy C Bonaparte
(74) Attorney, Agent, or Firm — Brinks Gilson & Lione

(57) ABSTRACT

A fluorine-containing ether monocarboxylic acid aminoalkyl ester represented by the general formula:

$$C_nF_{2n+1}O[CF(CF_3)CF_2O]_aCF(CF_3)COO(CH_2)_bNR^1R^2$$

(wherein $R^1$ is a hydrogen atom, an alkyl group having 1 to 12 carbon atoms, an aryl group, or an aralkyl group, preferably an alkyl group having 1 to 6 carbon atoms or an aryl group; $R^2$ is an alkyl group having 1 to 12 carbon atoms, an aryl group, or an aralkyl group, preferably an alkyl group having 1 to 6 carbon atoms or an aryl group; n is an integer of 1 to 3; a is an integer of 2 to 20, preferably an integer of 4 to 10; and b is an integer of 1 to 12, preferably an integer of 1 to 3). Such a fluorine-containing ether monocarboxylic acid ester having an amino group at the end of the ester group is produced by reacting a perfluoroether carboxylic acid fluoride compound $C_nF_{2n+1}O[CF(CF_3)CF_2O]_aCF(CF_3)COF$ and a hydroxyalkyl amine compound $HO(CH_2)_bNR^1R^2$ in the presence of an alkali metal fluoride.

4 Claims, No Drawings

FLUORINE-CONTAINING ETHER MONOCARBOXYLIC ACID AMINOALKYL ESTER AND A METHOD FOR PRODUCING THE SAME

RELATED APPLICATION

This application is a 35 U.S.C. § 371 national phase filing of International Patent Application No. PCT/JP2015/052992, filed Feb. 3, 2015.

TECHNICAL FIELD

The present invention relates to a fluorine-containing ether monocarboxylic acid aminoalkyl ester and a method for producing the same. More particularly, the present invention relates to a fluorine-containing ether monocarboxylic acid aminoalkyl ester that is imparted with flexibility in a molecular chain due to an ether bond in a molecule, and that is effectively used as a synthetic raw material, etc.; and also relates to a method for producing the same.

BACKGROUND ART

Heretofore, the present applicant has proposed various fluoroethers having a terminal alkylamino group, to which flexibility in the molecular chain is imparted by an ether linkage in the molecule, or fluorine-containing polyether carboxylic acid amides (see Patent Documents 1 to 7). Further, the present applicant has also proposed fluorine-containing acid fluoride compounds having COOH, CONH$_2$, or the like at the molecular end (see Patent Document 8).

However, there has been hardly observed finding on fluorine-containing ether carboxylic acid esters having an amino group at the end of the ester group.

PRIOR ART DOCUMENT

Patent Document

Patent Document 1: WO 2007/026513
Patent Document 2: JP-A-2008-255042
Patent Document 3: JP-A-2009-1709
Patent Document 4: JP-A-2010-254736
Patent Document 5: JP-A-2011-202055
Patent Document 6: JP-A-2011-213837
Patent Document 7: JP-A-2013-32455
Patent Document 8: JP-A-2008-255035
Patent Document 9: JP-A-3-284642
Patent Document 10: JP-A-62-270546

OUTLINE OF THE INVENTION

Problem to be Solved by the Invention

An object of the present invention is to provide a fluorine-containing ether monocarboxylic acid ester having an amino group at the end of ester group, and a method for producing the same.

Means for Solving the Problem

The above present invention provides a fluorine-containing ether monocarboxylic acid aminoalkyl ester represented by the general formula:

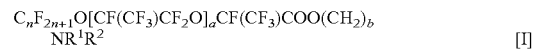
$$C_nF_{2n+1}O[CF(CF_3)CF_2O]_aCF(CF_3)COO(CH_2)_b NR^1R^2 \quad [I]$$

wherein $R^1$ is a hydrogen atom, an alkyl group having 1 to 12 carbon atoms, an aryl group, or an aralkyl group, preferably an alkyl group having 1 to 6 carbon atoms or an aryl group; $R^2$ is an alkyl group having 1 to 12 carbon atoms, an aryl group, or an aralkyl group, preferably an alkyl group having 1 to 6 carbon atoms or an aryl group; n is an integer of 1 to 3; a is an integer of 2 to 20, preferably an integer of 4 to 10; and b is an integer of 1 to 12, preferably an integer of 1 to 3.

Such a fluorine-containing ether monocarboxylic acid aminoalkyl ester is produced by reacting a perfluoroether carboxylic acid fluoride compound represented by the general formula:

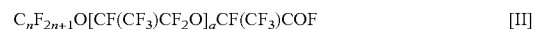
$$C_nF_{2n+1}O[CF(CF_3)CF_2O]_aCF(CF_3)COF \quad [II]$$

wherein n is an integer of 1 to 3; a is an integer of 2 to 20, preferably an integer of 4 to 10; and a hydroxyalkyl amine compound represented by the general formula:

$$HO(CH_2)_bNR^1R^2 \quad [III]$$

wherein $R^1$ is a hydrogen atom, an alkyl group having 1 to 12 carbon atoms, an aryl group, or an aralkyl group, preferably an alkyl group having 1 to 6 carbon atoms or an aryl group; $R^2$ is an alkyl group having 1 to 12 carbon atoms, an aryl group, or an aralkyl group, preferably an alkyl group having 1 to 6 carbon atoms or an aryl group; and b is an integer of 1 to 12, preferably an integer of 1 to 3; in the presence of an alkali metal fluoride.

Effect of the Invention

The present invention provides a fluorine-containing ether monocarboxylic acid aminoalkyl ester that is imparted with flexibility in a molecular chain due to an ether bond in the molecule, and that is effectively used as a synthetic intermediate for various substances, particularly for various substances for which flexibility is required, and that forms a flexible fluorine-containing polymer. The fluorine-containing ether monocarboxylic acid aminoalkyl ester is also available as a wear resistance improver (extreme-pressure additive) for various fluorine oils to be in contact with metal. Due to the water- and oil-repellency inherent therein, the fluorine-containing ether monocarboxylic acid aminoalkyl ester is used as a water- and oil-repellency agent in which the ester is supported on silica gel or metal.

EMBODIMENTS FOR CARRYING OUT THE INVENTION

The fluorine-containing ether monocarboxylic acid aminoalkyl ester [I] according to the present invention is produced by reacting a perfluoroether carboxylic acid fluoride compound [II] and a hydroxyalkyl amine compound [III] in the presence of an alkali metal fluoride.

The perfluoroether carboxylic acid fluoride compound [II] is represented by the general formula:

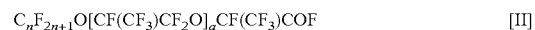
$$C_nF_{2n+1}O[CF(CF_3)CF_2O]_aCF(CF_3)COF \quad [II]$$

n: 1 to 3
a: 2 to 20, preferably 4 to 10
each of which is a known compound.

Specifically, Patent Document 9 discloses the compound wherein n is 1 or 2, and Patent Document 10 discloses the compound wherein n is 3. Moreover, these patent documents indicate that a is an integer of 0 or 1 or more, and specifically disclose the compound wherein a=0, which is a dimer of hexafluoropropene oxide [HFPO] that is a synthetic raw material thereof, the compound wherein a=1, which is a trimer of HFPO, the compound wherein a=2, which is a tetramer of HFPO, and the like.

Since these perfluoroether carboxylic acid fluoride compounds are easily reacted with water, the alkali metal fluoride used in the reaction is preferably calcined immediately before use to adjust the moisture content to 0.1 wt. % or less.

Examples of the hydroxyalkyl amine compound [III], which is preferably an ω-hydroxyalkyl amine compound, to be reacted with the perfluoroether carboxylic acid fluoride compound [II] include N-methylethanolamine, N,N-dimethylethanolamine, N-ethylethanolamine, N,N-diethylethanolamine, 3-(methylamino)-1-propanol, 3-(dimethylamino)-1-propanol, 4-(methylamino)-1-butanol, 4-(dimethylamino)-1-butanol, N-phenylethanolamine, N-phenylpropanolamine, N-p-toluylethanolamine, N-p-toluylpropanolamine, N-benzylethanolamine, N,N-dibenzylethanolamine, and the like.

These compounds [II] and [III] are stoichiometrically used at the same molar ratio; however, in practice, the compound [III] is generally used at a small excess molar ratio relative to the compound [II].

Moreover, examples of the alkali metal fluoride, which acts as a scavenger for hydrogen fluoride by-produced in the reaction, include sodium fluoride, potassium fluoride, cesium fluoride, rubidium fluoride, acidic sodium fluoride, acidic potassium fluoride, and the like. Sodium fluoride is suitably used in terms of price, availability, and handling during the reaction. The alkali metal fluoride is used in an amount of about 2 times mol per mol of the compound [II].

It is preferable to use a solvent in the reaction. Particularly preferred solvents are fluorine-containing solvents, such as HCFC-225 (dichloropentafluoropropane), HFE-449 (methoxy nonafluorobutane), HFE-569 (ethoxy nonafluorobutane), and 1,3-bis(trifluoromethyl)benzene. In practice, commercial products, such as AE-3000 and AK-225 (produced by Asahi Glass Co., Ltd.), Novec HFE (produced by Sumitomo 3M Ltd.), and Vertrel XF (produced by Du Pont-Mitsui Fluorochemicals Co., Ltd.), are suitably used.

Although the reaction temperature is not particularly limited, the reaction is preferably performed at a low temperature, particularly preferably at about 0 to 10° C., in terms of productivity.

After completion of the reaction, the alkali metal fluoride forming a complex with hydrogen fluoride by-produced in the reaction is removed by means such as filtration. The removing method is not particularly limited, and can be any filtration method selected from vacuum filtration, pressure filtration, centrifugal filtration, and the like.

Thereafter, washing with an alkali metal hydroxide aqueous solution having a dilute concentration is performed to remove hydrogen fluoride binding to amino groups present in the reaction mixture liquid. The alkali metal hydroxide is preferably sodium hydroxide or potassium hydroxide. The concentration of its aqueous solution is preferably more dilute; in particular, an aqueous solution having a concentration of about 1 to 5 wt. % is preferably used. Washing with this alkali metal hydroxide aqueous solution is preferably performed at a low temperature, particularly preferably at about 0 to 5° C., because hydrolysis progresses at a high temperature.

After washing with the alkali aqueous solution, the fluorine-containing solvent is removed under reduced pressure. The removing method is appropriately selected from a distillation device, an evaporator, a thin film dryer, etc., depending on the entire volume. The obtained reaction product is purified by removing impurities by molecular distillation or the like, to obtain the target product, i.e., a fluorine-containing ether monocarboxylic acid aminoalkyl ester.

The fluorine-containing ether monocarboxylic acid aminoalkyl ester, which is the desired product, is represented by the general formula:

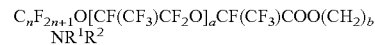
$$C_nF_{2n+1}O[CF(CF_3)CF_2O]_aCF(CF_3)COO(CH_2)_b NR^1R^2 \quad [I]$$

wherein a is an integer of 2 to 20, preferably an integer of 4 to 10.

This compound has water- and oil-repellency, and it is therefore required that the molecular weight of the polyfluoropolyether group $C_nF_{2n+1}[CF(CF_3)CF_2O]_aCF(CF_3)$— be 500 or more. Further, in consideration of solubility in solvents, etc., the preferred molecular weight is considered to be about 500 to 2000. From this viewpoint, the value of a is an integer of 2 to 20, preferably an integer of 4 to 10.

EXAMPLES

The following describes the present invention with reference to Examples.

Example 1

200 g (191 mmol) of $C_3F_7O[CF(CF_3)CF_2O]_4CF(CF_3)COF$ (95.0 GC %), 900 ml of a fluorine-containing solvent (Novec HFE-7200, produced by Sumitomo 3M Ltd.), and 16.0 g (381 mmol) of sodium fluoride were charged in a 1 L flask equipped with a stirring blade, a thermometer, a dropping funnel, and a reflux condenser in a nitrogen atmosphere. After the mixture was cooled to 50° C. or less in an ice bath, 17.9 g (201 mmol) of N,N-dimethylethanolamine (100 GC %) was slowly added dropwise from the dropping funnel, while maintaining the temperature at 10° C. or less.

After completion of the dropwise addition, the sodium fluoride was removed by a pressure filtering device, and the reaction mixture was then returned to the above reactor and cooled to 0° C. Then, 1000 g of a 2 wt. % NaOH aqueous solution, which had previously been cooled to 5° C., was slowly added thereto. After stirring the mixture for 15 minutes, the organic phase was collected and washed with 1000 g of 5° C. water. The fluorine-containing solvent in the organic phase was distilled off under reduced pressure by an evaporator, and a yellow, highly viscous residue was obtained. The highly viscous residue was subjected to simple distillation, thereby obtaining 189 g (yield: 93.2%) of the following fluorine-containing ether monocarboxylic acid aminoalkyl ester compound of a pale yellow, highly viscous liquid state.

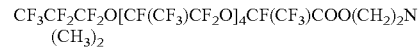
$$CF_3CF_2CF_2O[CF(CF_3)CF_2O]_4CF(CF_3)COO(CH_2)_2N(CH_3)_2$$

$^{19}$F-NMR (acetone-d6, CFCl$_3$ standard, ppm):
$^1$H-NMR (acetone-d6, TMS standard, ppm):

$$CF_3CF_2CF_2O[CF(CF_3)CF_2O]_4CF(CF_3)COO(CH_2)_2N(CH_3)_2$$

$^{19}$F-NMR (acetone-d6, CFCl$_3$ standard, ppm):

| δ = | −80.0~−85.6 | —CF₂O— | (m, 10F) |
|---|---|---|---|
| | −82.4 | —CF(CF₃)COO— | (s, 3F) |
| | −83.0 | —CF(CF₃)CF₂O— | (s, 3F) |
| | −83.2 | CF₃CF₂— | (s, 3F) |
| | −131.4 | CF₃CF₂CF₂O— | (s, 2F) |
| | −133.1 | —CF(CF₃)COO— | (t, 1F) |
| | −145.0~−145.9 | —CF(CF₃)CF₂O— | (m, 4F) |

¹H-NMR (acetone-d6, TMS standard, ppm):

| δ = | 4.30 | —OCH₂— | (t, 2H) |
|---|---|---|---|
| | 2.44 | —CH₂N— | (m, 2H) |
| | 2.28 | CH₃— | (s, 6H) |
| IR: | | 1792 cm⁻¹ | —C=O vibration |

Example 2

In Example 1, the reaction and purification were carried out using 200 g (105 mmol) of a compound represented by the following formula:

C₃F₇O[CF(CF₃)CF₂O]ₐCF(CF₃)COF a: 9.5 (NMR number average) as the perfluoroether carboxylic acid fluoride compound, and 17.9 g (175 mmol) of N-dimethylaminopropanol (100 GC %) as the hydroxyalkyl amine compound, thereby obtaining 153 g (yield: 73%) of the following fluorine-containing ether monocarboxylic acid aminoalkyl ester compound of a pale yellow, highly viscous liquid state.

CF₃CF₂CF₂O[CF(CF₃)CF₂O]ₐCF(CF₃)COO(CH₂)₃N(CH₃)₂ a: 9.5 (NMR number average)

¹⁹F-NMR (acetone-d6, CFCl₃ standard, ppm):

| δ = | −80.0, −85.6 | —CF₂O | (m) |
|---|---|---|---|
| | −82.3 | —CF(CF₃)COO— | (s, 3F) |
| | −83.1 | —CF(CF₃)CF₂O— | (s) |
| | −83.3 | CF₃CF₂— | (s, 3F) |
| | −131.4 | CF₃CF₂CF₂O— | (s, 2F) |
| | −133.1 | —CF(CF₃)COO— | (t, 1F) |
| | −145.0~145.9 | —CF(CF₃)CF₂O— | (m, 7.5F) |

¹H-NMR (acetone-d6, TMS standard, ppm):

| δ = | 4.28 | —OCH₂— | (t, 2H) |
|---|---|---|---|
| | 2.78 | —CH₂N— | (m, 2H) |
| | 2.28 | CH₃— | (s, 6H) |
| | 1.77 | —CH₂CH₂CH₂N— | (m, 2H) |
| IR: | | 1790 cm⁻¹ | —C=O vibration |

The invention claimed is:

1. A fluorine-containing ether monocarboxylic acid aminoalkyl ester represented by the general formula:

$$C_nF_{2n+1}O[CF(CF_3)CF_2O]_aCF(CF_3)COO(CH_2)_bNR^1R^2 \quad [I]$$

wherein $R^1$ is a hydrogen atom, an alkyl group having 1 to 12 carbon atoms, an aryl group, or an aralkyl group; $R^2$ is an alkyl group having 1 to 12 carbon atoms, an aryl group, or an aralkyl group; n is an integer of 1 to 3; a is an integer of 2 to 20; and b is an integer of 1 to 12.

2. The fluorine-containing ether monocarboxylic acid aminoalkyl ester according to claim 1, wherein a is an integer of 4 to 10, and b is an integer of 1 to 3.

3. A method for producing the fluorine-containing ether monocarboxylic acid aminoalkyl ester according to claim 1, comprising reacting a perfluoroether carboxylic acid fluoride compound represented by the general formula:

$$C_nF_{2n+1}O[CF(CF_3)CF_2O]_aCF(CF_3)COF \quad [II]$$

wherein n is an integer of 1 to 3, and a is an integer of 2 to 20; and a hydroxyalkyl amine compound represented by the general formula:

$$HO(CH_2)_bNR^1R^2 \quad [III]$$

wherein $R^1$ is a hydrogen atom, an alkyl group having 1 to 12 carbon atoms, an aryl group, or an aralkyl group; $R^2$ is an alkyl group having 1 to 12 carbon atoms, an aryl group, or an aralkyl group; and b is an integer of 1 to 12; in the presence of an alkali metal fluoride.

4. The method for producing the fluorine-containing ether monocarboxylic acid aminoalkyl ester according to claim 3, wherein after completion of the reaction, the reaction mixture is treated with an alkali metal hydroxide aqueous solution.

* * * * *